(12) United States Patent
Porter

(10) Patent No.: US 9,907,975 B1
(45) Date of Patent: Mar. 6, 2018

(54) THERAPEUTIC LASER TREATMENT AND TRANSDERMAL STIMULATION OF STEM CELL DIFFERENTIATION

(71) Applicant: Roger D. Porter, Loris, SC (US)

(72) Inventor: Roger D. Porter, Loris, SC (US)

( * ) Notice: Subject to any disclaimer, the term of this patent is extended or adjusted under 35 U.S.C. 154(b) by 174 days.

(21) Appl. No.: 14/547,920

(22) Filed: Nov. 19, 2014

(51) Int. Cl.
A61N 5/067 (2006.01)
A61N 5/06 (2006.01)

(52) U.S. Cl.
CPC ......... *A61N 5/0613* (2013.01); *A61N 5/0622* (2013.01); *A61N 2005/067* (2013.01); *A61N 2005/0643* (2013.01)

(58) Field of Classification Search
CPC .... A61N 5/062; A61N 5/0616; A61N 5/0622; A61N 2005/067
USPC ...................................... 607/88, 89; 128/898
See application file for complete search history.

(56) References Cited

U.S. PATENT DOCUMENTS

| | | |
|---|---|---|
| 3,769,963 A | 11/1973 | Goldman et al. |
| 3,913,582 A | 10/1975 | Sharon |
| 4,069,823 A | 1/1978 | Isakov et al. |
| 4,215,694 A | 8/1980 | Isakov et al. |
| 4,640,283 A | 2/1987 | Sawa et al. |
| 4,669,839 A | 6/1987 | Muchel |
| 4,671,285 A | 6/1987 | Walker |
| 4,672,969 A | 6/1987 | Dew |
| 4,686,986 A | 8/1987 | Fenyo et al. |
| 4,697,590 A | 10/1987 | Naki et al. |
| 4,724,835 A | 2/1988 | Liss et al. |
| 4,854,320 A | 8/1989 | Dew et al. |
| 4,930,504 A | 6/1990 | Diamantopoulos et al. |
| 4,930,505 A | 6/1990 | Hatje |
| 4,966,144 A | 10/1990 | Rochkind et al. |
| 5,002,051 A | 3/1991 | Dew et al. |
| 5,021,452 A | 6/1991 | Labbe et al. |
| 5,029,581 A | 7/1991 | Kaga et al. |
| 5,049,147 A | 9/1991 | Danon |
| 5,050,597 A | 9/1991 | Daikuzono |

(Continued)

OTHER PUBLICATIONS

PowerPoint presentation entitled "High Intensity Laser Therapey (HILT) for the treatment of cartilage lesions of the knee," cited in U.S. Patent Application No. 2007/0185552.

(Continued)

*Primary Examiner* — Ahmed Farah
(74) *Attorney, Agent, or Firm* — Smith Moore Leatherwood LLP; Thomas W. Epting

(57) ABSTRACT

A method for transdermally treating selected tissue and/or for facilitating the release and/or differentiation of stem cells, including exposing the selected tissue to laser light having a wavelength between approximately 600 and 1400 nm, and maintaining such exposure of the selected tissue or bone to the laser light for a period of time sufficient to deliver a laser light dosage of at least 3 Joules/cm$^2$ per treatment and maintaining such exposure for a period of time sufficient to deliver a laser light dosage of at least 1000 Joules per treatment within a 24 hour period of time. The method also includes upcollimating the laser light such that the laser delivers to the selected tissue a substantially coherent beam of laser light having a cross-sectional area of at least 5 cm$^2$, and, further, delivering the laser light to a depth of at least 5 mm in the selected tissue.

6 Claims, 1 Drawing Sheet

(56) References Cited

U.S. PATENT DOCUMENTS

| | | |
|---|---|---|
| 5,051,823 A | 9/1991 | Cooper et al. |
| 5,150,704 A | 9/1992 | Tatebayashi et al. |
| 5,259,380 A | 11/1993 | Mendes et al. |
| 5,320,619 A | 6/1994 | Badawi |
| 5,344,434 A | 9/1994 | Talmore |
| 5,409,479 A | 4/1995 | Dew et al. |
| 5,409,482 A | 4/1995 | Diamantopoulos |
| 5,445,146 A | 8/1995 | Bellinger |
| 5,445,608 A | 8/1995 | Chen et al. |
| 5,464,436 A | 11/1995 | Smith |
| 5,514,168 A | 5/1996 | Friedman |
| 5,527,350 A | 6/1996 | Grove et al. |
| 5,616,140 A | 4/1997 | Prescott |
| 5,649,924 A | 7/1997 | Everett et al. |
| 5,707,403 A | 1/1998 | Grove et al. |
| 5,755,752 A | 5/1998 | Segal |
| 5,785,702 A | 7/1998 | Murphy-Chutorian et al. |
| 5,792,215 A | 8/1998 | Martin et al. |
| 5,807,881 A | 9/1998 | Leong et al. |
| 5,951,596 A | 9/1999 | Bellinger |
| 6,033,431 A | 3/2000 | Segal |
| 6,063,108 A | 5/2000 | Salansky et al. |
| 6,066,129 A | 5/2000 | Larson |
| 6,084,242 A | 7/2000 | Brown, Jr. et al. |
| 6,090,101 A | 7/2000 | Quon et al. |
| 6,100,290 A | 8/2000 | Levy et al. |
| 6,140,984 A | 10/2000 | Kanazawa et al. |
| 6,156,028 A | 12/2000 | Prescott |
| 6,162,211 A | 12/2000 | Tankovich et al. |
| 6,165,205 A | 12/2000 | Neuberger |
| 6,221,068 B1 | 4/2001 | Fried et al. |
| 6,267,779 B1 * | 7/2001 | Gerdes ................ A61N 5/0616 606/3 |
| 6,267,780 B1 | 7/2001 | Streeter |
| 6,273,883 B1 | 8/2001 | Furumoto |
| 6,273,905 B1 | 8/2001 | Streeter |
| 6,283,956 B1 | 9/2001 | McDaniel |
| 6,290,714 B1 | 9/2001 | Streeter |
| 6,302,900 B1 | 10/2001 | Riggs |
| 6,312,451 B1 | 11/2001 | Streeter |
| 6,354,297 B1 | 3/2002 | Eiseman |
| 6,413,267 B1 | 7/2002 | Dumoulin-White et al. |
| 6,454,791 B1 | 9/2002 | Prescott |
| 6,494,900 B1 | 12/2002 | Salansky et al. |
| 6,503,268 B1 | 1/2003 | Neurberger et al. |
| 6,527,764 B1 * | 3/2003 | Neuberger ............ A61N 5/0616 606/10 |
| 6,527,797 B1 | 3/2003 | Masotti et al. |
| 6,554,824 B2 | 4/2003 | Davenport et al. |
| 6,569,156 B1 | 5/2003 | Tankovich et al. |
| 6,592,611 B1 | 7/2003 | Zawanda |
| 6,600,951 B1 | 7/2003 | Anderson |
| 6,629,971 B2 | 10/2003 | McDaniel |
| 6,663,659 B2 | 12/2003 | McDaniel |
| 6,676,654 B1 | 1/2004 | Balle-Petersen et al. |
| 6,676,655 B2 | 1/2004 | McDaniel |
| 6,746,473 B2 | 6/2004 | Shanics et al. |
| 6,845,112 B2 | 8/2005 | Sumida et al. |
| 7,033,348 B2 | 4/2006 | Alfano et al. |
| 7,081,128 B2 | 7/2006 | Hart et al. |
| 7,094,252 B2 | 8/2006 | Koop |
| 7,118,563 B2 | 10/2006 | Weckwerth et al. |
| 7,160,287 B1 | 1/2007 | Siegel |
| 7,177,695 B2 | 2/2007 | Moran |
| 7,217,265 B2 | 5/2007 | Hennings et al. |
| 7,303,578 B2 | 12/2007 | De Taboada et al. |
| 7,328,708 B2 | 2/2008 | Malak |
| 7,331,953 B2 | 2/2008 | Manstein et al. |
| 7,351,252 B2 | 4/2008 | Altshuler et al. |
| 7,604,630 B2 | 10/2009 | Jun |
| 8,033,284 B2 | 10/2011 | Porter et al. |
| 8,316,860 B1 | 11/2012 | Porter et al. |
| 2001/0034517 A1 | 10/2001 | Masotti et al. |
| 2002/0002391 A1 | 1/2002 | Gerdes |
| 2002/0025225 A1 | 2/2002 | Segal |
| 2003/0004499 A1 | 1/2003 | McDaniel |
| 2003/0004556 A1 | 1/2003 | McDaniel |
| 2003/0114902 A1 | 6/2003 | Prescott |
| 2003/0167080 A1 | 9/2003 | Hart et al. |
| 2003/0181962 A1 | 9/2003 | Streeter |
| 2004/0006378 A1 * | 1/2004 | Shanks ................ A61N 5/0616 607/89 |
| 2004/0010300 A1 | 1/2004 | Massotti et al. |
| 2004/0167500 A1 | 8/2004 | Weckwerth et al. |
| 2004/0210275 A1 | 10/2004 | Town et al. |
| 2004/0260367 A1 | 12/2004 | De Taboada et al. |
| 2005/0015077 A1 | 1/2005 | Kuklin et al. |
| 2005/0049582 A1 | 3/2005 | DeBenedictis et al. |
| 2005/0065577 A1 | 3/2005 | McArthur et al. |
| 2005/0107852 A1 | 5/2005 | Levernier et al. |
| 2005/0137656 A1 | 6/2005 | Malak |
| 2005/0177093 A1 | 8/2005 | Hart et al. |
| 2005/0197681 A1 * | 9/2005 | Barolet ................ A61B 18/203 607/86 |
| 2005/0215987 A1 | 9/2005 | Slatkine |
| 2005/0222555 A1 | 10/2005 | Manstein et al. |
| 2005/0234383 A1 | 10/2005 | Dougal |
| 2005/0234527 A1 | 10/2005 | Slatkine |
| 2005/0245998 A1 | 11/2005 | Pruitt et al. |
| 2005/0256554 A1 | 11/2005 | Malak |
| 2005/0283145 A1 | 12/2005 | Malak |
| 2006/0009823 A1 | 1/2006 | Richardson et al. |
| 2006/0013533 A1 | 1/2006 | Slatkine |
| 2006/0095101 A1 | 5/2006 | Dees et al. |
| 2006/0259102 A1 | 11/2006 | Slatkine |
| 2007/0032847 A1 | 2/2007 | Weckwerth et al. |
| 2007/0100401 A1 | 5/2007 | Lin |
| 2007/0101785 A1 | 5/2007 | Peckham et al. |
| 2007/0106284 A1 | 5/2007 | Siegel |
| 2007/0162093 A1 * | 7/2007 | Porter ................ A61N 5/0613 607/89 |
| 2007/0185552 A1 | 8/2007 | Masotti |
| 2007/0260297 A1 | 11/2007 | Chariff |
| 2008/0033412 A1 | 2/2008 | Whelan et al. |
| 2008/0033513 A1 | 2/2008 | Man et al. |
| 2008/0058784 A1 | 3/2008 | Manstein et al. |
| 2008/0140023 A1 | 6/2008 | McMillan |
| 2008/0234669 A1 | 9/2008 | Kauvar |
| 2009/0069872 A1 | 3/2009 | Fortuna et al. |
| 2009/0105790 A1 | 4/2009 | Bornstein |
| 2009/0216219 A1 | 8/2009 | Ventar et al. |
| 2011/0060266 A1 * | 3/2011 | Streeter ................ A61N 5/0613 604/20 |
| 2012/0076830 A1 * | 3/2012 | Sitharaman ............ B82Y 5/00 424/400 |
| 2013/0041309 A1 * | 2/2013 | Siegel ................ A61N 5/0616 604/20 |
| 2014/0039581 A1 * | 2/2014 | Oron ................ A61N 5/0618 607/89 |

OTHER PUBLICATIONS

PowerPoint presentation entitled "Safety and Efficacy of near Infrared Light for Cartilage Re-growth of Deep Osteochondral Defect in Sheelp as Animal Mode," cited in U.S. Patent Application No. 2007/0185552.

Notification of Transmittal of the International Search Report and the Written Opinion of the International Searching Authority, or the Declaration dated Oct. 1, 2007, for International Application No. PCT/US07/00786.

Chow, Robert T., Barnsley, Les, "Systematic Review of the Literature of Low-Level Laser Therapy (LLLT) in the Management of Neck Pain," Lasers in Surgery and Medicine, 2005, pp. 46-52, vol. 37.

Karu, Tina, "Primary and Secondary Mechanisms of Action of Visible to Near-IR Radiation on Cells," Journal of Photochemistry and Photobiology B: Biology, 1999, pp. 1-17, 49.

Wilden, Lutz and Karthein, Rainer, "Import of Radiation Phenomena of Electrons and Therapeutic Low-Level Laser in Regard to the Mitochondrial Energy Transfer," Journal of Clinical Laser Medicine Surgery, 1998, No. 3, vol. 16, pp. 159-165.

(56) References Cited

OTHER PUBLICATIONS

Tuby, H., Maltz, L., Oron, U., "Induction of autologous mesenchymal stem cells in the bone marrow by low-level laser therapy has profund beneficial effects on the infarcted rat heart," Lasers Surg Med. Jul. 2011;43(5):401-9, http://www.ncbi.nlm.nih.gov/pubmed/21674545.

Gonzalez-Lima, F. and Barrett, Douglas W., "Augmentation of cognitive brain functions with transcranial lasers," Frontiers in Systems Neuroscience Mar. 2014, vol. 8, Article 36.

Arany, PR, et al., "Photoactivation of endogenous latent transforming growth factor-β1 directs dental stem cell differentiation for regeneration," Sci Transl Med., May 2014, http://www.ncbi.nlm.nih.gov/pubmed/24871130.

* cited by examiner

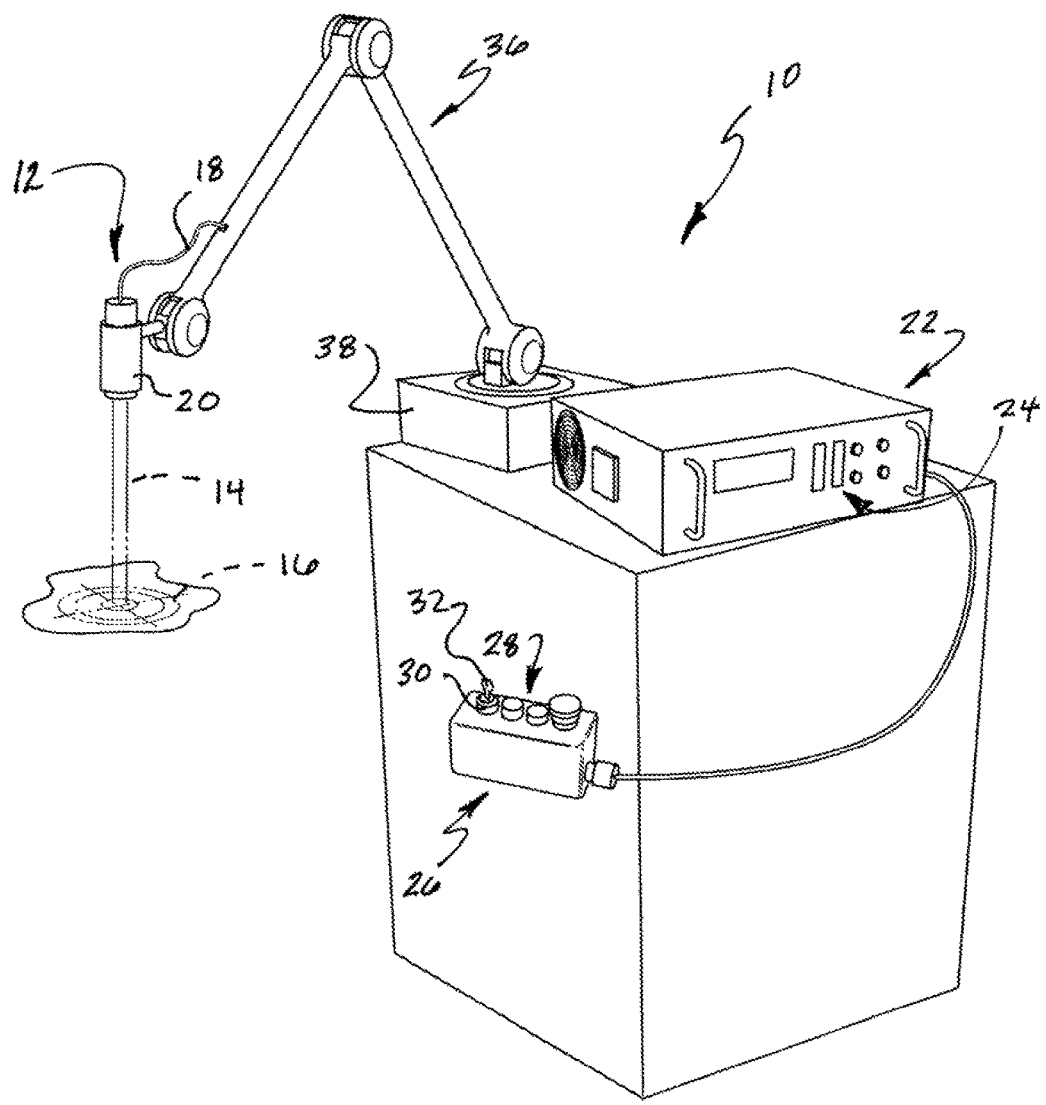

THERAPEUTIC LASER TREATMENT AND TRANSDERMAL STIMULATION OF STEM CELL DIFFERENTIATION

FIELD

The present invention relates to methods and apparatus for treating biological tissues using therapeutic laser techniques and, in particular, to using such methods and apparatus for the stimulation of differentiation of stem cells, and more specifically, to selectively generating stem cells by transdermal laser exposure of bone marrow.

BACKGROUND

Lasers provide monochromatic light, and have found a number of uses in the field of medicine. Monochromatic light coming from a laser is of the same wavelength, and the coherent characteristic of laser light typically refers to the waves making up the laser light having the same direction, amplitude, and phase with respect to one another.

Lasers used for medical treatments typically fall into several groups. For example, "hot" lasers are typically used in surgery, and "mid-power" lasers may be used in photodynamic therapy for cancer treatment, dermatological treatments, etc. "Low energy" lasers generally deliver significantly less energy to tissue than surgical lasers and mid-power, and accordingly, produce relatively little heat in biological tissue such that the tissue is not subjected to thermal damage. Low energy lasers have been used for dermatology treatments, traumatology, and in other areas for enhancing healing and providing therapeutic benefits in certain applications.

Optical energy produced by lasers may have beneficial and healing effects when applied to living tissues. In certain laser therapy procedures, optical energy reacts with tissue cells, potentially producing positive effects on cellular functions and healing processes.

It may be desirable to maximize the non-thermal, biostimulative effects of optical energy on tissues while minimizing unwanted and potentially damaging thermal effects.

SUMMARY

Laser therapy consistent with the present disclosure may be characterized as producing beneficial effects by differentiation of mesenchymal stem cells (MSCs), also known as marrow stromal cells, within the stroma of bone marrow. Cellular differentiation is the process by which a less specialized cell may become a more specialized cell type, a process which can convert MSCs into a variety of cell types such as osteoblasts, chondrocytes, myocytes, adipocytes, and beta-pancreatic islets cells.

Generally, the present invention includes methods and apparatus for treating selected tissue for the purpose of stimulating differentiation of stem cells in skeletal tissue such as, for example, femoral bone marrow, cranial bone marrow, sternum bone marrow, pelvic bone marrow, and spine bone marrow. Methods described herein include promoting stem cell differentiation in bone marrow tissue by at least providing a laser light source that delivers a beam of monochromatic coherent light at least 600 nm, providing an aiming beam and aiming the aiming beam at bone marrow tissue to define a target in the bone marrow tissue, collimating the beam of monochromatic coherent laser light into a beam of collimated monochromatic coherent light having a cross-sectional area of at least 5 $cm^2$, and transdermally exposing an area of at least 5 $cm^2$ of the patient's skin proximate the target to the depth of the target in the bone marrow tissue with the beam of collimated monochromatic coherent light at a power density of approximately 500 $mW/cm^2$ at the patient's skin for a time sufficient to deliver at least 3 $Joules/cm^2$ and at least 1,000 total Joules to the tissue per treatment, as measured at the patient's skin.

In another aspect, the present invention includes methods and apparatus for stimulation of brain function. Methods described herein comprise providing a laser light source that delivers a beam of monochromatic coherent light at about 1064 nm, providing an aiming beam, aiming the aiming beam at cranial tissue to define a target in the tissue, collimating the beam of monochromatic coherent laser light into a beam of collimated monochromatic coherent light having a cross-sectional area of at least 5 $cm^2$, and transdermally exposing an area of at least 5 $cm^2$ of the patient's skin proximate the target in the tissue to a depth corresponding to cranial bone marrow in the tissue with the beam of collimated monochromatic coherent light at a power density of approximately 500 $mW/cm^2$ for a time sufficient to deliver at least 3 $Joules/cm^2$ and at least 1,000 total Joules to the tissue per treatment, as measured at the patient's skin.

In a further aspect, the present invention includes a method for augmenting cognitive brain function. Methods described herein comprise providing a laser light source that delivers a beam of monochromatic coherent light at about 1064 nm, providing an aiming beam, aiming the aiming beam at brain tissue to define a target in the brain tissue, collimating the beam of monochromatic coherent laser light into a beam of collimated monochromatic coherent light having a cross-sectional area of at least 5 $cm^2$, and transdermally exposing an area of at least 5 $cm^2$ of the patient's skin proximate the target in the brain tissue to a depth of at least 5 mm within the brain tissue with the beam of collimated monochromatic coherent light at a power density of approximately 500 $mW/cm^2$ for a time sufficient to deliver at least 3 $Joules/cm^2$ and at least 1,000 total Joules to the tissue per treatment, as measured at the patient's skin.

The methods may further comprise providing a probe connected to the laser light source that outputs the beam of collimated monochromatic coherent light, wherein the transdermal exposing of the target in the tissue with the collimated monochromatic coherent light includes pressing the probe against the patient's skin.

By carefully controlling the direction of laser emission, the power density of the optical energy as well as the treatment area and time, the present invention is believed to provide positive therapeutic effects associated with increased stimulation and differentiation of stem cells related to the use of high dosages of biostimulating energy, while avoiding unwanted thermal effects.

These and other implementations are described in greater detail in the detailed description which follows.

BRIEF DESCRIPTION OF THE DRAWINGS

Having thus described exemplary aspects of the disclosure in general terms, reference will now be made to the accompanying drawings, which are not necessarily drawn to scale, and wherein:

The FIGURE illustrates a perspective view of an example apparatus for providing therapeutic laser treatment constructed in accordance with the present invention.

DETAILED DESCRIPTION

The foregoing, as well as other objects of the present invention, will be further apparent from the following detailed description of the preferred embodiment of the invention, when taken together with the accompanying drawing and the description which follows set forth this invention in its preferred embodiment. However, it is contemplated that persons generally familiar with the use of lasers for medical treatment will be able to apply the novel characteristics of the structures and methods illustrated and described herein in other contexts by modification of certain details. Accordingly, the drawing and description are not to be taken as restrictive on the scope of this invention, but are to be understood as broad and general teachings.

Referring now to the drawing in detail, an apparatus for therapeutic laser treatment in accordance with the present invention is indicated generally in the FIGURE by reference character 10.

In the FIGURE, a laser system, generally 10, for conducting therapeutic laser treatment is shown, and includes a laser, which, in one preferred embodiment, is a neodymium doped yttrium-aluminum-garnet (Nd:YAG) laser or a neodymium doped yttrium vanadate (Nd:YVO4) laser device, or probe, generally, 12, which emits a laser beam 14. Laser device 12 preferably delivers optical radiation in the form of laser light at a wavelength of between 600 and 1400 nanometers (nm) (although wavelengths of 400 to 10,000 nm could also be used, and provides a laser beam 14 in the range from 1 mW/cm$^2$ to at least 500 mW/cm$^2$. Laser system 10 is configured such that treatment times for exposing human and/or animal tissue can be varied from one second or less to continuous, i.e., 24 hours a day for the desired number of days, or portions thereof. Treatments in accordance with the present invention preferably range between 1 Joules/cm$^2$ to 200 Joules/cm$^2$, and most preferably involve in most cases transdermally exposing the tissue to a range between 3 and 40 Joules/cm$^2$ of laser exposure and maintaining the transdermal exposure of the selected tissue to the laser light for a period of time sufficient to deliver a laser light dosage to the tissue of a range between 1,000 and 32,000 Joules per treatment within a 24 hour period. In certain applications, for example, when treating fever blisters, fibromyalgia, etc., treatments within a 24 hour period may exceed 32,000 Joules, and such treatments may be repeated daily.

In one preferred embodiment, laser device 12 has a wavelength of 1064 nanometers in the near infrared region of the electromagnetic spectrum. The energy of the optical radiation is controlled and applied to produce a minimum absorption rate in the irradiated tissue to minimize elevation of the average temperature of the irradiated tissue to a level above the basal body temperature and in no event to the extent the maximum absorption rate is great enough to convert the irradiated tissue into a collagenous substance.

It has been determined through extensive testing that the foregoing condition is satisfied by a Nd:YAG laser operated at its fundamental wavelength of 1064 nanometers at a power output level of from 100-1000 milliwatts/cm$^2$, with the laser beam being focused to produce a power density of the projected laser beam in the range of from about 100 mW/cm$^2$ to about 1000 mW/cm$^2$.

Laser system 10 could also include, if desired, an aiming laser (not shown) to facilitate use in aiming the laser beam 14 of laser device, generally 12, at a target, generally 16. Target 16 is a generalized representation the desired treatment area of human or animal tissue to be irradiated by laser beam 14, in a manner described below. For the purposes of the present disclosure, "aiming" an optical device, such as an aiming laser, at a selected tissue such as skeletal tissue can comprise or include directing the laser or other optical emission device toward the selected tissue and/or intermediary tissues or surfaces disposed between the optical emission or laser source and the selected tissue. For example, aiming an aiming laser at cranial skeletal tissue can include aiming the laser at intermediary tissue such as epithelial layers. Further, aiming an aiming laser at, for example, femoral skeletal tissue can include aiming the aiming laser at epithelial, muscular, or other intermediary tissue layers between the optical emission or laser source and the selected femoral skeletal tissue.

A collimator 20 is connected to laser 12 in order to allow the size of laser beam 14, carried by fiber optic cable 18, to be increased, while still maintaining and enhancing the coherency and monochromacity of laser beam 14. Preferably, by selection of an appropriate collimator 20 and/or through the use of multiple collimators, the beam size can be changed from ½ cm$^2$ to a cross-sectional output usable in treating the entire body of the patient by using one or more collimators large enough to expose the entire body of the patient simultaneously (except for areas which do not require and/or should not receive laser treatment exposure, such as the patient's eyes, etc.) and/or by moving laser 12 in a grid-like pattern during treatment of the patient. It is to be understood, however, that while laser system 12 is illustrated herein as using a fiber optic cable 18, a series of mirrors (not shown) could be used instead of, or in combination with, cable 18 to direct the laser beam 14 to target 16, if desired.

Alternately, instead of using a collimator, it is believed that a laser device could be provided having an output beam with a cross-sectional area of 2 to 10 cm$^2$ or more, without exceeding an output of 600 mW/cm$^2$ Laser system 10 also includes a power supply, control unit, and resonator, collectively generally 22, having a control panel, generally 24, for controlling the operation output of laser device 12. Unit 22 preferably includes a processor for allowing for preprogrammed laser treatments to be executed using laser device 12, such programs being selectable from control panel 24 having a keypad or other data entry device. Also, in one preferred embodiment, a foot pedal (not shown) and/or a handheld controller, generally 26, is connected to laser device 12 having controls, generally 28, for allowing a healthcare provider, technician, etc., to control laser 12 remotely from control panel 24, if desired. Controller 26 may include a keyed lock-out switch 30 having a key 32 in order to prevent unauthorized operation of laser device 12. Instead of, or in addition to a key 32, control box 28 could include a keypad (not shown) for entering a desired treatment protocol to be delivered by laser device 12 and/or for allowing a personal identification number (PIN), authorization codes, biometric identifier such as a fingerprint reader, etc., to be entered by a healthcare provider or technician in order to operate laser device 12, if desired. Also, controller 26 could be wirelessly connected to control unit 22, as could also laser device 12.

Laser device 12 is, in one preferred embodiment, connected to an articulated arm 36 which allows for flexibility in manipulating and aiming laser device 12 at a particular target. It is to be understood, however, that laser system 10 is not limited to articulated arm 36, and could be mounted in a variety of other configurations, if desired, and/or be handheld by the healthcare provider, if desired.

Furthermore, it is to be understood that the present invention is not limited to the laser device 12 shown, but could be a variety of other sizes, as could also collimator 20, and could be configured for exposing a target 16 of a variety of sizes, including a full body exposure of a patient. Articulated arm 36 is mounted on base 38, although it could be mounted on a wall, ceiling, floor, examination table, etc., if desired. Also, laser system 10 could be portable, such that it may be carried by hand, and/or mounted on a wheeled cart, or other base, for facilitating transport within a medical facility, in the field, or in other environments.

The present invention includes methods and protocols for using laser energy at elevated dosages in order to achieve therapeutic benefit while refraining from damaging the tissue being treated. In practicing the methods of the present invention, the nature and extent of the tissue disorder is first diagnosed and the location, size, and number of treatment area(s) is established. Thereafter, the treatment area(s) is transdermally exposed to monochromatic, coherent light below the level necessary to cause thermal damage to the tissue being treated, wherein the light is in the near infrared portion of the electromagnetic spectrum. The treatment area is transdermally exposed to the monochromatic, coherent light for a sufficient treatment time to produce clinically beneficial effects by delivering a dosage typically greater than 3 Joules/cm$^2$.

As discussed above, monochromatic light refers to light which is of the same wavelength, and coherent means that the waves of light have similar direction, amplitude, and phase to each other. In accordance with one preferred embodiment of the present invention, monochromatic, coherent light having a wavelength in the 600 to 1400 nanometer (nm) range is used in the treatment of soft tissue, bone, and/or body fluids and other disorders by irradiating a treatment area for sufficient time to produce clinically beneficial effects. It is contemplated dosages in the range of approximately 3 Joules/cm$^2$ to approximately 40 Joules/cm$^2$ are preferred, although even higher dosages could be given without departing from the spirit of the present invention.

In one preferred method of the present invention, a dosage of approximately 3 Joules/cm$^2$ is delivered to the tissue. Additional treatments and treatment areas may be treated as determined by the diagnosing physician or other health care provider.

The wavelength of laser light is the basic electromagnetic wave feature directly linked to the energy of an individual light quantum (photon). Cell culture experiments have indicated that there is selectivity in photo-induced phenomena related to wavelengths. Wavelengths in the range of preferably between 600 to 1400 nm are used in the present invention, although wavelengths in the range of 400 to 10,000 nm could also be used, depending on the particular treatment. Since tissue optical parameters (reflection, scattering, refraction, absorption and depth penetration) depend on wavelength, a particular light wavelength may affect three-dimensional light distribution in tissue. For example, in a specific wavelength range, the longer wavelength the more light penetration depth.

Intensity is the rate of light energy delivery to 1 cm$^2$ of skin or other tissue. Intensity is measured in milliWatts per cm$^2$ (mW/cm$^2$). Suitable intensities for biostimulation are known to be in the range of from 0.1 to 1,000 mW/cm$^2$. As used herein, the term "dose" means the light energy provided to the unit of surface (1 cm$^2$) of target 16 during a single irradiation and measured in J/cm$^2$ or mJ/cm$^2$.

By way of example, a laser generating 10 Watts of output power may be used to deliver optical energy to a 20 cm$^2$ treatment area. This produces an intensity, or power density, of 500 mW/cm$^2$, which is currently the maximum intensity permitted by the U.S. Food and Drug Administration (FDA). It is to be understood, however, that in the event the FDA raises or lowers the maximum allowable intensity, or if the present invention is used in locations where regulations otherwise permit, the methods and apparatus as disclosed herein can be modified as necessary without departing from teachings of the present invention. There are other optical parameters, including the type of the light source, optical power, intensity, dose, frequency and pulse duration, wavelength and bandwidth, beam diameter and divergence, three-dimensional light distribution, etc. which may be selected to provide an optimized protocol to treat the disorder.

The method in accordance with the present invention is adapted for the therapeutic treatment of any of a patient's tissue, which includes muscle, nerve, bone, body fluids (including spinal fluid), epithelial, and/or connective tissues. In accordance with a preferred embodiment, the method is adapted for the relief of acute and chronic soft tissue trauma or disorder and to provide musculoskeletal pain management. Such methods can be adapted to provide treatment directed towards the patient's soft tissue, nerve, epithelial, and or connective tissues. Additionally, as discussed throughout the present disclosure, such methods can be adapted or directed towards the treatment of skeletal tissue in order to stimulate the release and/or differentiation of stem cells such as MSCs. To this end, any skeletal tissue can be treated not inconsistent with the objectives of the present invention. For example, skeletal tissue to be treated can include cranial, spinal, femoral (skeletal tissue associated with the femur or femurs), dental, or other skeletal tissues such as pelvic bones and the sternum. In certain embodiments, any skeletal tissue containing bone marrow and/or MSC-containing stroma can be used consistent with methods described herein.

A wide range of disorders of biological tissue or their symptoms may be treated by laser system 10 and a wide range of augmentative procedures may be provided by laser system 10, including the following:

1. Musculo-skeletal conditions, such as: degenerative joint disease, traumatic joint and ligament injury, such as rotator cuff, ankle sprain, knee strain, tennis elbow, golf elbow, TMJ, muscle contusions, bone fracture, fibromyalgia, and costochondritis;

2. Neurological conditions, such as: peripheral neuropathy, reflex sympathetic dystrophy, trigeminal neuralgia, migraine headache, stroke, concussions, plantar fasciitis, radiculophthy, spinal injury, peripheral neuropathy, sciatica, traumatic nerve injury, diabetic nerve, restless leg syndrome, and tension and migraine headache;

3. Wound treatment such as: post op healing, decubitis wound sores, burns (first degree and full thickness); stasis ulcers, allergic rashes (example, poison ivy etc.), and insect bites;

4. Pain management, such as: spinal pain from herniated or bulging disc, back pain from musculoskeletal strain, reflex symphatic dystrophy, fibromyalgia, pain from musculo-skeletal items listed; and 5. Viral infections, such as: herpes, all types (including mononucleosis) and acquired immune deficiency syndrome (AIDS); and autoimmune diseases, such as: multiple sclerosis, psoriasis, rhumatoid diseases, chronic fatigue syndrome, Parkinson's disease, and lupus.

6. Augmentation of cognitive brain function associated with frontal cortex functions such as sustained attention, working memory, and affective state.

Treatment in accordance with the present invention is also anticipated to meet with success in treatment of other neurological conditions, such as: stroke, closed head injury, and spinal cord injury; in cardio vascular system conditions, such as: coronary artery disease and peripheral vascular disease; in viral infection applications, such as viral flu syndromes; and in connection with autoimmune diseases, such as diabetes, ALS, and others.

In accordance with one preferred embodiment of the present invention, the tissue to be treated is irradiated with optical energy. Not intending to be bound by theory, the treatment is believed to activate an endogenous latent growth factor complex that subsequently differentiates host MSCs to promote tissue regeneration upon application of methods described herein to stroma in adjacent and/or corresponding skeletal tissue.

In accordance with one preferred embodiment, a diode-pumped, solid-state Nd:YAG laser is used as the source of this optical energy, producing optical energy in the form of light at 1064 nm wavelength. This light is guided through fiber optic cable 18 collimator 20 with an aperture sized appropriately for the desired treatment area and the time necessary to cover the treatment area. In accordance with one embodiment, the aperture of collimator 20 is circular, with an area of 0.5 cm$^2$ to an area sufficient to simultaneously treat the whole body of a patient and this embodiment is particularly adapted for application to a treatment target site of approximately 28 cm$^2$.

While laser system 10 is contemplated for use in accordance with the present invention, those skilled in the art will appreciate the variety of other laser systems which may be utilized without departing from the teachings of the present invention. By way of non-limiting examples, representative methods of the present invention are disclosed below.

After diagnosing the nature and extent of a tissue disorder, the physician preferably establishes the location, size, and number of treatment areas. In one embodiment, the size of the treatment areas is approximately 10 cm$^2$, although the treatment area may range from between approximately 0.1 cm$^2$ to entire body of the patient. Where different treatment sites are contemplated, the laser aperture is accordingly adjusted to accommodate the different treatment site sizes, and the treatment sites are treated by transdermally exposing them to monochromatic, coherent light from laser device 12. Larger areas may be treated by moving laser device 12 and collimator over the entire area in a grid-like fashion.

It is contemplated the duration for treatment time can be continuous, i.e., up to 24 hours per day, over several days, if necessary. It will be appreciated by those skilled in the art that the treatment may be a single treatment or may be repeated daily, or periodically for a prescribed number of days necessary to produce clinically beneficial effects.

The relationship between various wavelengths of light and the depth of penetration into the patient's tissues has been demonstrated by others. The choice of wavelength used is dependent upon the depth required to treat the affected tissues. For example, depth of penetration can be selected to penetrate to or through bone marrow tissue of a selected skeletal tissue, or can be selected for a predetermined value, such as between about 1 and about 10 mm, for example about 5 mm.

A single laser device 12 can be used for tender points, trigger points, selected points in the affected area, points on the skin overlying the treatment target (e.g. tendon, spur, calcification deposit), spinal nerve roots, points on the skin overlying selected nerve pathways and other localized (e.g. acupuncture) points.

If desired, laser device 12 of the present invention may be constructed of flexible plastic (not shown) or other suitable material to be wrapped around the surface contours of the body. Alternatively, the laser device may be formed in the shape of a ring (not shown), having light sources arranged on its inner surface, to apply treatment to a finger or other extremity.

There are different techniques for performing the treatment methods of the present invention, depending on the application. In the contact technique, laser device 12 is applied directly to the skin surface. In the contact with pressure technique, laser device 12 is applied to the skin surface with pressure. This technique of pressing the probe against the patient's skin allows deeper light penetration to the tissue, since light scattering is generally significantly less in compressed tissue, and light absorption by blood is less because blood is partially squeezed out of the compressed tissue.

The scanning technique is used for the treatment of large areas with laser devices. In practicing the scanning technique, the laser device is moved by the health care provider along the skin surface with definite speed and the affected area is irradiated by a laser beam. This technique is used when the area to be treated is large, and preferably involves use of one or more collimators 20.

The use of monochromatic, collimated laser light at approximately 1064 nm, at an intensity of 500 mW/cm$^2$, is believed to allow the beneficial effects of laser light to penetrate deeper than heretofore practiced, in that the laser light is not so readily absorbed and dissipated prior to reaching the targeted tissue, which may reach down to the bone.

The majority of treatments in accordance with the present invention involve transdermally exposing the tissue to at least 3 Joules/cm$^2$ of laser exposure for a period of time sufficient to deliver a laser light dosage of at least 1000 Joules to the tissue, per treatment within a 24 hour period. In certain applications, for example, when treating peripheral neuropathy, fibromyalgia, etc., treatments within a 24 hour period may exceed 32,000 Joules, and such treatments may be repeated daily.

More specifically, one aspect of the present invention includes a method for augmenting cognitive brain function by using laser device 12 to deliver a beam of monochromatic coherent light at about 1064 nm. An aiming laser (not shown) may be provided for delivering an aiming beam, which is aimed transdermally at brain tissue to define a target in the brain tissue. The method may include collimating the beam of monochromatic coherent laser light into a beam of collimated monochromatic coherent light having a cross-sectional area of at least 5 cm$^2$, as measured at the patient's skin, and transdermally exposing an area of at least 5 cm$^2$ of the patient's skin proximate the target in the brain tissue to a depth of at least 5 mm within the brain tissue, with the beam of collimated monochromatic coherent light being at a power density of approximately 500 mW/cm$^2$ for a time sufficient to deliver at least 3 Joules/cm$^2$ and at least 1,000 total Joules to the tissue per treatment as measured at the patient's skin.

In the foregoing methods, the power density, treatment area, treatment time, and/or total treatment dosage may be selected to facilitate the release and/or differentiation of stem cells. Additionally, a probe connected to the laser light source that outputs the beam of collimated monochromatic coherent light, wherein the transdermal exposing of the target in the tissue with the collimated monochromatic coherent light includes pressing the laser device, or probe, 12 against the patient's skin in order to allow deeper light penetration to the tissue, given that the amount of light scattering is generally significantly less in compressed tissue, and, accordingly, light absorption by blood is less because blood is partially squeezed out of the compressed tissue.

Following are examples of the present invention, all of which use laser light at 1064 nm wavelength at an intensity of at 500 mW/cm², but it is to be understood that the present invention is not limited to such examples and that such examples are presented herein for non-limiting, illustrative purposes:

EXAMPLES

Example 1

A 50 year old male presented with a 2-year history of severe pain in feet. He had previously been treated by multiple physicians and podiatric physicians with multiple modality treatment regimens, all without relief of symptoms. These symptoms were primarily pain at night and on early rising. Despite those treatments, the patient, who was on his feet all day as a freight delivery person, was in constant pain. He presented for treatment by referral and was given a total of approximately ten minutes of treatment with a laser over the soles of his feet. After a second treatment of approximately five minutes, the patient was pain-free. He has remained in that state to date without further treatments, and has continued his normal work schedule.

Example 2

The patient presented with chronic neck pain and unable to raise his hands above 90 degrees in the lateral plane without significant pain. He had been to numerous clinics in the past, including pain clinics, chiropractors, etc. without relief. A physical examination revealed bilateral tenderness in both subscapular areas, as well as moderate swelling of the soft tissues. The treatment with a laser included the patient receiving 2 treatments bilaterally along the subscapular region, with total treatment time being approximately 20 minutes in length. There was a five day separation in treatment protocols. The results were that after the third treatment day, there was a 90% reduction in pain with motion, and after the tenth treatment day of treatment, the patient stated he was free of pain and had no movement restrictions.

Example 3

The patient was presumed to have chronic arthritic pain, as no neurological symptoms were present, and an MRI showed no disc disease. The patient had less than 30 degrees of rotation to the left and 45 degrees to the right. The patient received 10 treatments of approximately 20 minutes each to the cervical areas three through seven. At the end of the treatment, the patient had 80 degrees of rotation bilaterally.

Example 4

The patient presented with pain in the left knee, and the diagnosis was that the pain was caused by an old ACL injury which had not been repaired. Pre-treatment parameters included 30 degree flexion and significant pain with ambulation, especially when walking stairs. The patient also experienced difficult ambulation upon rising in the morning. The treatment protocol included the patient receiving ten 20 minute treatments. He received five consecutive treatments, followed by five days without treatment, and then five more similar treatments. Post treatment measurements yielded flexion at 95 degrees with no pain in climbing stairs, no early morning pain, and generally unlimited ambulation.

Example 5

The patient presented two years out post-op for lumbar disc disease. No further surgery was suggested. He was referred for pain relief using the laser protocols. The patient was free of all objective findings, other than the surgical incisions. He complained of severe hyperesthesia over his entire right foot, especially the lateral aspect. The pain was severe enough to cause him to awaken at night when the bed sheets touched his foot. The treatment included the patient receiving a total of ten treatments consisting of five minutes to the L4-S1 segment of the lumbar spine, as well as five minutes to the areas of hyperesthesia on the right foot. The result was that after completion of the seventh treatment, the patient noted complete resolution of all pain and tenderness.

Example 6

A 60 year old male physician presented with an undiagnosed peripheral neuropathy which manifested with symptoms including loss of sensation and prior perception of his lower extremities. The patient was a prominent physician and on the board of major university medical system, and had undergone multiple tests with numerous specialists. No specific diagnosis was ever established except "peripheral neuropathy". This problem had been present for over 15 years, and the doctor felt that his symptoms were progressing. The treatment protocol consisted of daily exposure to the laser over the entire length of his spinal cord, as well as over the lumbar plexus. Each session lasted approximately 30 minutes. The length of the total sessions was five days, followed by 10 days of rest, and the process was then repeated. After the second cycle of treatments, the patient reported a significant change is his ability to "feel" his legs. Before the treatment, he could not walk on the beach because he could not tell where his feet were and would fall constantly. Also, before the treatment he could walk on the concrete surface of his pool deck and not feel any heat, and now he must wear shoes to avoid painful burning sensation. He could also walk on the beach without fear of falling.

Example 7

A 55 year old female who was 20 years post-op from an ankle reconstruction, presented with severe ankle pain on the operative ankle. She had multiple screws implanted at the time of surgery. Since then she was in constant pain and could only wear running shoes with the back of the shoes cut out. She could not climb stairs without significant discomfort. Several surgical consultations were sought, and the only advice she was given was a total ankle fusion, which she rejected. She received a total of three treatments to the entire ankle of approximately ten minutes per treatment. She has been free of pain for the last 60 days, and is back wearing normal shoes.

From the foregoing, it will be obvious to those skilled in the art that various modifications in the above-described method and apparatus can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

What is claimed is:

1. A method for promoting stem cell differentiation and/or stem cell generation in bone marrow tissue, the method comprising:
    providing a laser light source that delivers a beam of monochromatic coherent light having a wavelength of about 1064 nm;
    directing the beam of monochromatic coherent light towards a skin surface to transdermally aim the beam of monochromatic coherent light at bone marrow tissue that is underlying the skin surface;
    collimating the beam of monochromatic coherent laser light into a beam of collimated monochromatic coherent light having a cross-sectional area greater than 12.5 cm$^2$; and
    transdermally exposing the bone marrow tissue with the beam of collimated monochromatic coherent light, the bone marrow tissue being located at a depth of at least 2.7 mm below the skin surface, and the collimated monochromatic coherent light having a power density greater than approximately 500 mW/cm$^2$ for a time sufficient to deliver greater than 5 Joules/cm$^2$ and at least 1,000 total Joules to the tissue being treated per treatment as measured at the skin surface.

2. The method of claim 1 further comprising providing a probe connected to the laser light source that outputs the beam of collimated monochromatic coherent light, wherein transdermally exposing the bone marrow tissue with the collimated monochromatic coherent light includes pressing the probe against the skin surface.

3. The method of claim 1, wherein the power density, treatment area, treatment time, and/or total treatment dosage is selected to facilitate the generation of stem cells.

4. The method of claim 1, wherein the bone marrow tissue comprises femoral bone marrow, cranial bone marrow, sternum bone marrow, pelvic bone marrow, and/or spine bone marrow.

5. A method for augmenting cognitive brain function in a patient, the method comprising:
    providing a laser light source that delivers a beam of monochromatic coherent light at about 1064 nm;
    directing the beam of monochromatic coherent light towards a skin surface to transdermally aim the beam of monochromatic coherent light at brain tissue that is underlying the skin surface;
    collimating the beam of monochromatic coherent laser light into a beam of collimated monochromatic coherent light having a cross-sectional area greater than 12.5 cm$^2$; and
    transdermally exposing the brain tissue with the beam of collimated monochromatic coherent light, the brain tissue being located at a depth of at least 5 mm below the skin surface, and the beam of collimated monochromatic coherent light having a power density greater than approximately 500 mW/cm$^2$ for a time sufficient to deliver greater than 5 Joules/cm$^2$ and at least 1,000 total Joules to the brain tissue per treatment as measured at the skin surface.

6. The method of claim 5 further comprising providing a probe connected to the laser light source that outputs the beam of collimated monochromatic coherent light, wherein the exposing the brain tissue with the collimated monochromatic coherent light includes pressing the probe against the skin surface.

* * * * *